United States Patent
Bride-Flynn

(10) Patent No.: US 6,470,705 B2
(45) Date of Patent: Oct. 29, 2002

(54) DISPOSABLE ICE PACK

(76) Inventor: Kelly L. Bride-Flynn, 27255 Hickory Hill Rd., Brooksville, FL (US) 34602

( * ) Notice: Subject to any disclaimer, the term of this patent is extended or adjusted under 35 U.S.C. 154(b) by 0 days.

(21) Appl. No.: 09/737,323

(22) Filed: Dec. 14, 2000

(65) Prior Publication Data

US 2002/0073731 A1 Jun. 20, 2002

(51) Int. Cl.$^7$ .............................. F25D 3/08; A61F 7/00
(52) U.S. Cl. ..................... 62/530; 62/457.2; 62/371; 607/108; 607/112
(58) Field of Search .................. 62/530, 457.2, 62/259.3, 420, 371; 607/96, 108, 119, 111, 112

(56) References Cited

U.S. PATENT DOCUMENTS

| | | | |
|---|---|---|---|
| 1,567,931 A | * 12/1925 | Epler | |
| 1,711,876 A | 5/1929 | Dorsey | |
| 1,819,913 A | 8/1931 | Miller et al. | |
| 1,927,751 A | 9/1933 | Mensi | |
| 2,865,420 A | * 12/1958 | Allenbach | |
| 3,889,684 A | * 6/1975 | Lebold | |
| 4,316,070 A | * 2/1982 | Prosise et al. | |
| 4,628,932 A | 12/1986 | Tampa | |
| 4,951,666 A | * 8/1990 | Inman et al. | |
| 5,074,300 A | 12/1991 | Murphy | |
| 5,133,348 A | 7/1992 | Mayn | |
| 5,277,180 A | * 1/1994 | Angelillo et al. | 607/114 |
| 5,356,426 A | * 10/1994 | Delk et al. | 607/112 |
| 5,456,704 A | 10/1995 | Kilcullen | |
| 5,716,388 A | * 2/1998 | Petelle | 607/108 |
| 6,251,131 B1 | * 6/2001 | Kohout | 607/114 |

\* cited by examiner

*Primary Examiner*—Chen-Wen Jiang
(74) *Attorney, Agent, or Firm*—Larson & Larson, P.A.; James E. Larson

(57) ABSTRACT

A disposable ice pack for treating an area of a person's body that has been traumatized or inured is disclosed. The ice pack includes a polyethylene bag portion having a sealable open top end, a pair of side edges and a closed bottom end forming an inner cavity. The inner cavity receives ice. A closure mechanism is disposed along an inner surfaces of the bag portion top end and provides a water tight seal for the ice pack. A pair of fluid absorbable material sheets are attached by a heat seal along the side edges and bottom end to the bag portion. The sheets of fluid absorbable material permit the disposable ice pack to soak-up any body fluids seeping from the traumatized area. An alternate embodiment further includes a plurality of tie-straps for permitting the ice pack to be wrapped around a person's body part. The tie-straps are attached by the heat seal.

20 Claims, 4 Drawing Sheets

DISPOSABLE ICE PACK

BACKGROUND OF THE INVENTION

1. Field of the Invention

The present invention relates generally to ice packs. More particularly, it relates to a disposable ice pack having a liquid absorbable material disposed about outer walls for applying to a wounded body part wherein body fluids, such as blood, may be seeping from the wound.

2. Description of the Prior Art

Ice and heat packs are known in the prior art. Both devices are known to assist in medical care for bruises, cuts, swelled joints, muscular strain and the like. For instance, it is known that the application of heat assists in muscular strain once swelling has reduced at the point of strain. Accordingly, hot water bottles can be used to apply heat directly to the muscular strained area. U.S. Pat. Nos. 1,711,876 and 1,819,913 both describe hot water bottle devices which can be used for heat treatment. Hot water is poured into these devices and closed, whereafter the device can be applied directly to a muscular strain.

At least one prior art invention suggests a device which can accommodate both heat or ice. In particular, U.S. Pat. No. 1,927,751 discloses a cover for a hot water bag or ice bag. This device employs straps which can be used to secure the device to a patient.

The use of ice to reduce swelling and inflammation of a wounded body area of a person is known to assist in the healing of that area. When trauma inflicts a body part, such as a knee, for example, swelling and inflammation of that area can occur. Inflammation is the result of the body introducing additional blood flow to the traumatized area. Additional blood flow assists in the healing of the wounded area by carrying away damaged or dead tissue. Swelling is the body's way of providing a "natural splint" to the traumatized area. Unfortunately both inflammation and swelling can cause additional pain to the person due to the force exerted upon the traumatized area. It is therefore advantageous to reduce the swelling and inflammation, and hence the need to apply ice to the inflicted body part.

Devices to assist in the reduction of inflammation and swelling are known. For instance, U.S. Pat. No. 4,628,932 describes an ice pack for use on a person's knee. Two compartments are employed to receive the ice. This device is helpful in the reduction of inflammation and swelling to a person's knee but is unfortunately limited in many ways. For instance, the device is limited for use on joints such as knees and elbows and lacks the structural components to be adaptable to other body parts. Further, it lacks an outer layer which could be used to reduce the temperature of the outside of the bag, which would make the bag more comfortable to hold by a person, and further lacks an absorbable material layer which could soak-up body fluids which may seep from the wounded area. This device could be wrapped in a dish towel. However, if any body fluids seep from the wound (i.e., blood), the dish towel would then need to be thrown away. This results in added expense and waste of a perfectly good towel. A person could instead wrap paper towels around the bag, but this too can add expense. Further, paper towels typically do not provide amble resistance from the coldness of the ice pack.

Some inventions have attempted to add an outer layer to their respective ice bag or heat pack. Such can be seen in U.S. Pat. Nos. 5,074,300, 5,133,348 and 5,456,704.

Unfortunately, all of these inventions fall short of disclosing, let alone teach of suggest, a disposable ice pack having a fluid absorbable outer layer which soaks-up any body fluids of the wound and at the same time permits a person to hold the ice pack to the wound without being uncomfortable to hold due to the coldness of the ice pack. Such a device is clearly needed to overcome all of the deficiencies of the prior art.

SUMMARY OF THE INVENTION

I have invented an improved ice pack for use in treating body part wounds. My device is disposable, inexpensive to manufacture and autoclavable. The device includes a bag portion made to retain ice or a frozen ice pack made of a chemical composition enclosed within a soft pliable shell. The bag portion is constructed from a material which precludes or significantly limits moisture from soaking therethrough. A soft and sanitary fluid absorbable material is employed along opposed outer walls of the bag portion. In a preferred embodiment, the fluid absorbable material is attached to the bag by a heat seal along at least two side edges. The fluid absorbable material is capable of absorbing body fluids which may seep from a traumatized body part. The fluid absorbable material also reduces the transfer of heat thereby making the bag more comfortable to hold against the body part by a person's hand such t hat it does not get too cold. It further assists in eliminating any sweating that may occur from the bag portion.

The bag portion has a top open end for permitting the ice cubes or frozen ice pack to be inserted therewithin. A water-tight closure mechanism is provided along the top open end and permits the ice pack to be closed such that nothing falls from out of the bag portion.

A set of tie-straps can be included for permitting the ice pack to be tied to person's body part, such as, for example, a knee. The tie-straps are held in place in between the an outer wall of the bag portion and bottom surface of the fluid absorbable material by the heat seal.

Accordingly, it is an object of the present invention to provide an improved ice pack which is disposable, inexpensive to manufacture and autoclavable.

It is a further object to provide an improved ice pack which can absorb fluids which may seep from a traumatized body part while the ice pack is employed.

It is still a further object to provide an improved ice pack which reduces the transfer of heat thereby making it more comfortable to hold against the body when in use.

It is still yet a further object to provide an improved ice pack which can have alternate tie-straps for permitting the ice pack to be attached to a person's wounded body part without the need to hold the ice pack by hand.

Other objects, aspects and uses will be appreciated when consideration is taken herein of the below set forth drawings, detailed description and claims.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
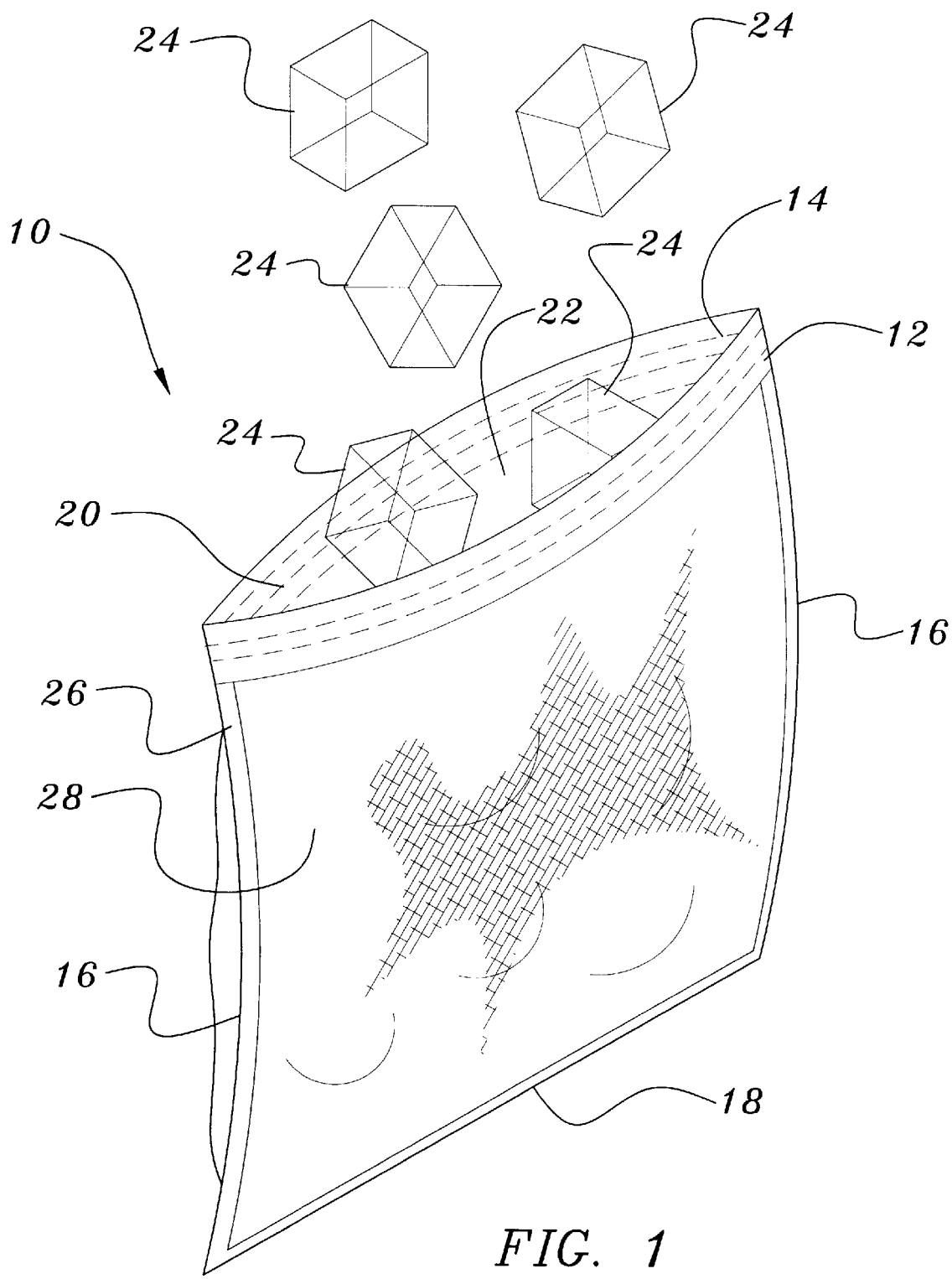
FIG. 1 is a perspective view of the novel disposable ice pack of the present invention, illustrating how ice cubes can be inserted through an open end and retained within a cavity of the pack.

Throughout the following detailed description, the same reference numerals refer to the same elements in all figures.

Referring to FIG. 1, an improved disposable ice pack 10 of the present invention is shown. Ice pack 10 is generally square-shaped and includes a bag portion 12 having an open top end 14, a pair of closed side edges 16 and a closed bottom end 18. Open top end 14 is provided with a closure mechanism 20. In the preferred embodiment, closure mechanism 20 employs a re-sealable closure configuration typically seen in the product known under the trademark Zip-Lock®. Closure mechanism 20 provides a water tight seal to ice pack 10 and further prohibits anything inserted therewithin from falling out when closure mechanism 18 is sealed.

With continuing reference to FIG. 1, bag portion 12 and its respective open top end 14, side edges 16 and closed bottom end 18 forms an inner cavity 22 which is used to retain ice cubes 24 or a freezable chemical composition having a pliable outer shell, such as an ice pack (not shown).

Figure 2:
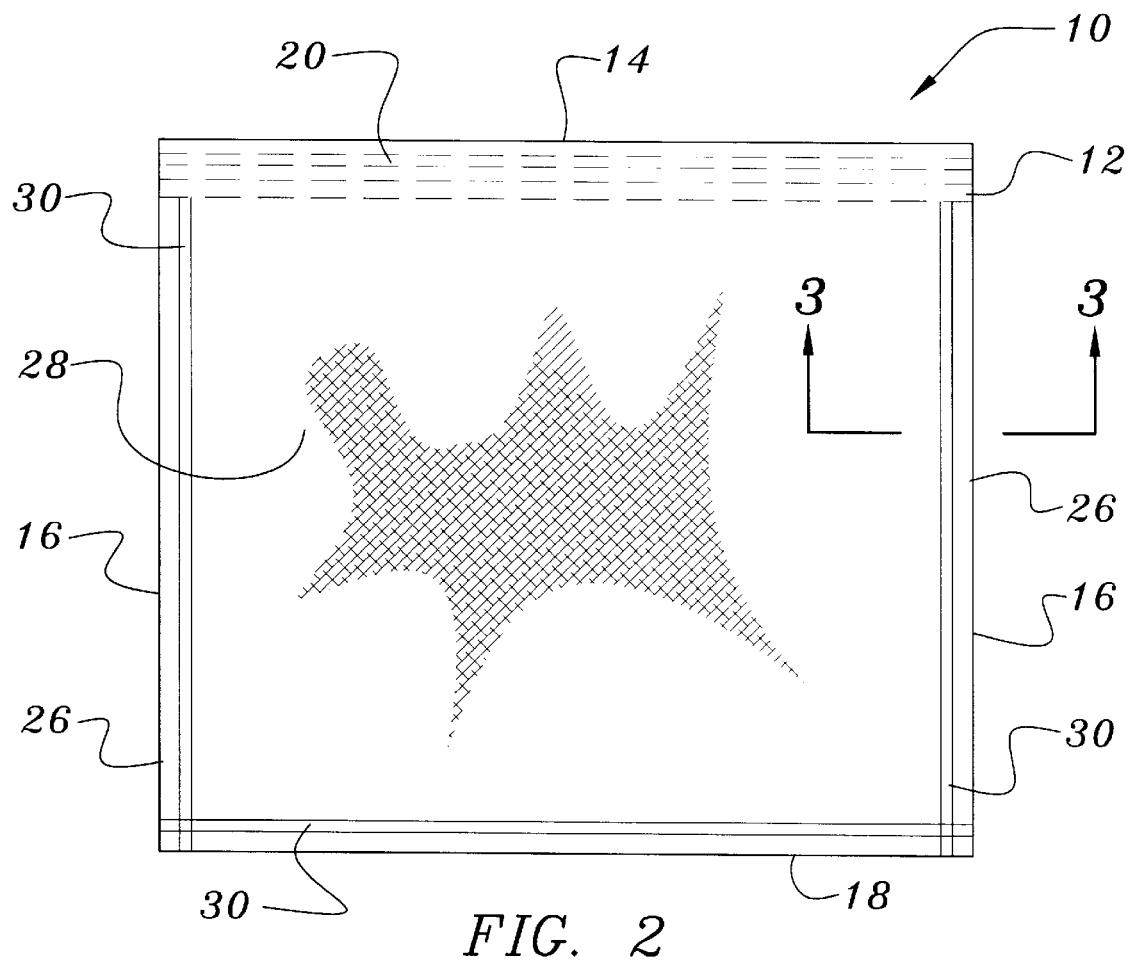
FIG. 2 is a front elevational view thereof.
Figure 3:
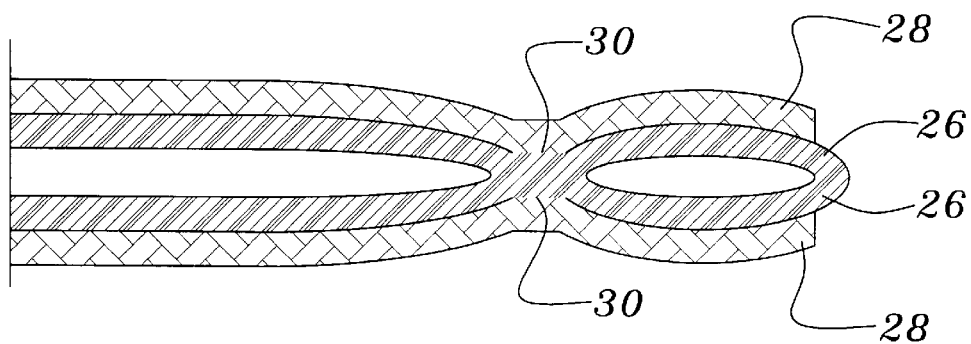
FIG. 3 is a cross-sectional view along lines 3—3 of FIG. 2.

Referring to FIG. 3, it is shown that bag portion 12 has opposed outer walls 26 on which a sheet of fluid absorbable material 28 is attached juxtaposed to each bag portion outer wall 26 by a heat seal 30. Accordingly, in the preferred embodiment, the present invention utilizes at least a pair of heat seal points proximal to bag portion side edges 16 (see FIG. 2). However, a third heat seal point, disposed proximal to bag portion closed bottom end 18 can also be employed to provide a greater adherence of each sheet of fluid absorbable material 28 to each bag portion outer wall 26 as illustrated in FIG. 3. In both embodiments, however, the heat seal points 30 run parallel to the respective side edge 16 or bottom end 18. In the preferred embodiment, the width of each heat seal point 30 is about 0.09" and the distance between an outer edge of each heat seal 30 to the respective bag portion side edge 16 or bottom end 18 is about 0.12". Although not shown, an alternate embodiment of the present invention could include a bag portion 12 having a single sheet of fluid absorbable material 28 on one bag portion outer wall 26.

Figure 4:
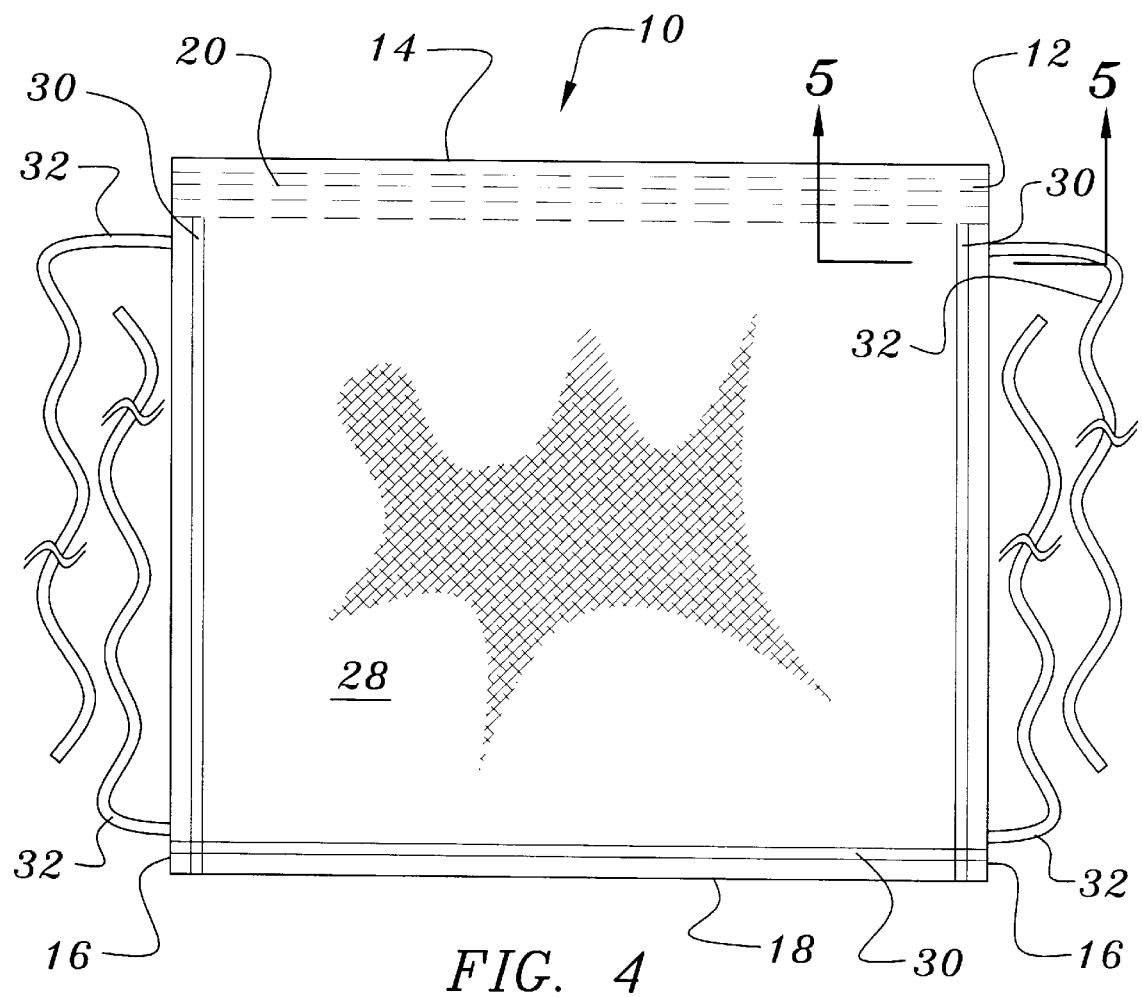
FIG. 4 is a front elevational view of an alternate embodiment of the present invention having a plurality of tie-straps for attaching the ice pack to a body part.
Figure 5:
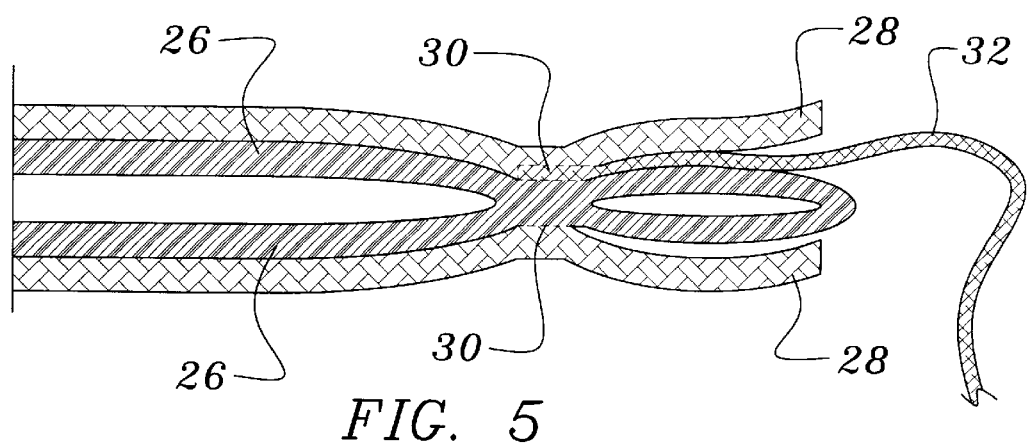
FIG. 5 is a cross-sectional view along lines 5—5 of FIG. 4.
Figure 6:
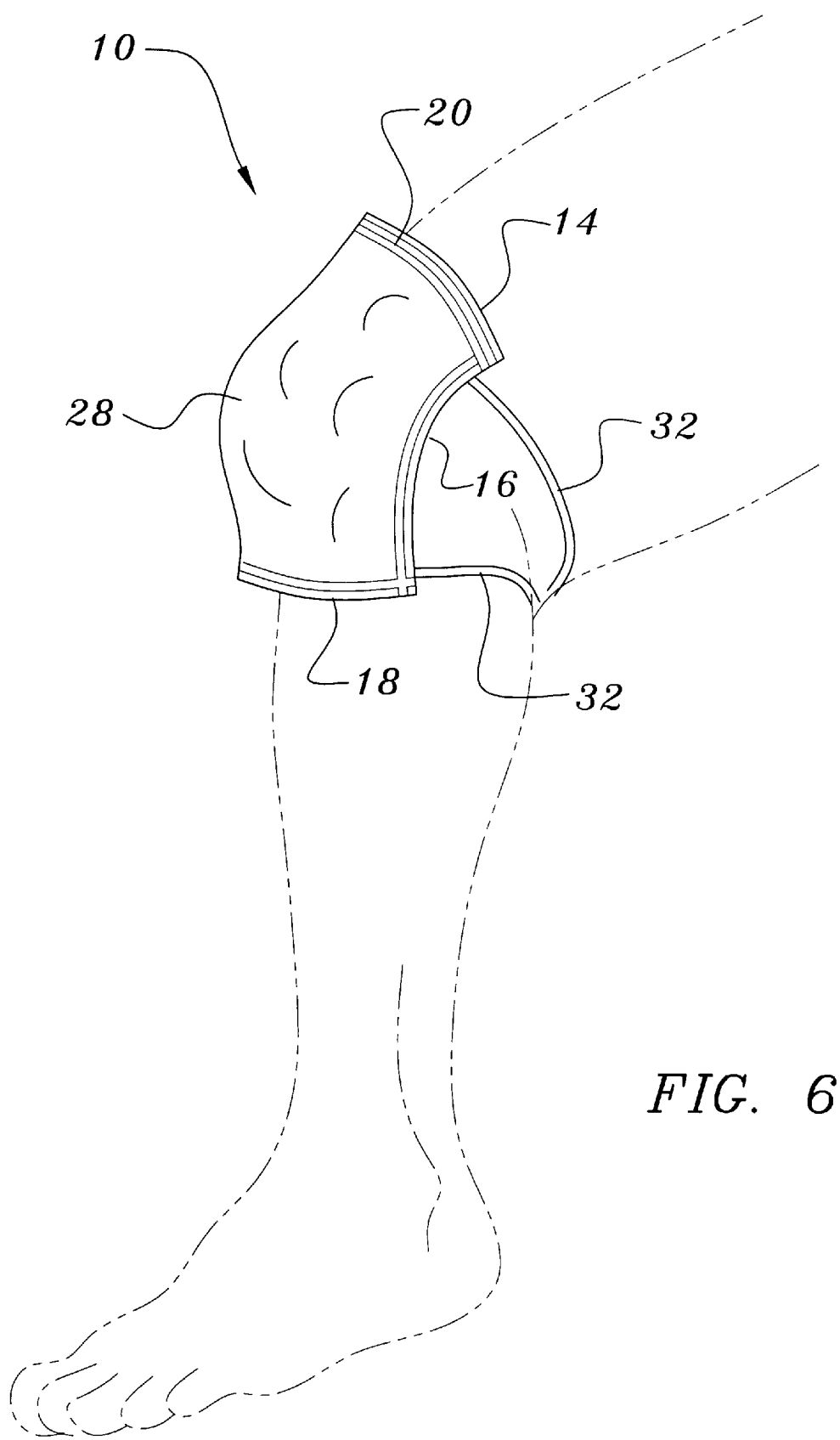
FIG. 6 is a perspective view of the alternate embodiment of the present invention employed around a knee cap of a person.

Referring to FIG. 4, an alternate embodiment of the present invention is shown. In such alternate embodiment, ice pack 10 includes all the features of the preferred ice pack, as fully discussed hereinabove, with the addition of a plurality of tie-straps 32. In the preferred embodiment of ice pack 10 having tie-straps 32, four tie-straps 32 are employed. One of each of the tie-straps 32 is attached at one of each of four corners 34 of bag portion 12. As shown in FIG. 5, each tie-strap 32 is attached in between a bottom surface of the sheet of fluid absorbable material 28 and an outer surface of the bag portion outer wall 26 by the heat seal 30. Tie-straps 32 are made from a soft flexible material so that it is comfortable to a person if employed around a body part. In such a scenario, for example, as shown in FIG. 6, tie-straps 32 can be used to employ ice pack 10 around a person's knee.

In the preferred embodiment, bag portion 12 should be constructed from a material which prohibits or least minimizes moisture from soaking through outer walls 26. For example, polyethylene can be used for bag portion 12. Since ice pack 10 is meant to be disposable it would be advantageous to construct bag portion from a material which breaks down quickly in the environment. Further to the preferred embodiment, the sheets of fluid absorbable material 28 should possess a high absorption quality. A two fiber cloth material is preferred for the sheets of fluid absorbable material 28 such that a first fiber is constructed of alpha-cellulose and the a second fiber is constructed of polyester. If so desired, the two fiber material can employ a two color configuration, for example, blue and white. If such a case, the second fiber (polyester) can be made of blue ink and contain cellulose acetate sorbate.

Further to the preferred embodiment, a heat weld is used to seal the sheets of fluid absorbable material 28 to the bag portion outer walls 26. A seam sealer can be used to accomplish the heat weld. For large production runs, a seam sealer tool specifically designed to the exact dimensions of the ice pack 10 would be most efficient and economical. Further, if the thickness of each bag portion outer wall 26 is generally equal to the thickness of each sheet of fluid absorbable material 32, a better heat seal 30 can be made. In the preferred embodiment, the thickness of bag portion 12 is in the range of 1¼ mils to 2½ mils, with 2½ mils being the preferred thickness.

Equivalent elements can be substituted for the ones set forth above such that they perform the same function in the same way for achieving the same result.

Having thus described the invention what is claimed and desired to be secured by Letters Patent is:

1. A disposable ice pack for receiving and retaining a frozen material and for compressing against an area of a person's body that has been traumatized, the disposable ice pack consisting of:
    a) a bag portion having four side edges, including a sealable open top end, a closed bottom end and a pair of opposed side edges forming an inner cavity, a closure mechanism disposed along inner surfaces of the top end providing a water tight seal to the ice pack, and a pair of outer walls, each side edge disposed at an adjacent side edge at a ninety-degree angle;
    b) sheet material having four side edges and consisting of one or two layers of fluid absorbable two fiber cloth material attached by heat sealing and juxtaposed to one of the bag portion outer walls, the one or two sheets of fluid absorbable material having a dimension slightly less than an outer wall of the four edge bag portion such that each side edge of the sheet material is positioned adjacent and parallel to one of the bag portion four side edges at a distance which is equal around all four side edges of the sheet material and bag portion, the absorbable material making contact with the person's traumatized body area and absorbing any body fluids seeping therefrom; and
    c) the inner cavity receiving and retaining the frozen material.

2. The disposable ice pack of claim 1, wherein the bag portion is generally square-shaped.

3. The disposable ice pack of claim 1, wherein the bag portion is constructed of polyethylene.

4. The disposable ice pack of claim 1, wherein the sheet material of fluid absorbable material is constructed of a two fiber cloth comprising a first fiber of alpha-cellulose and a second fiber of polyester.

5. The disposable ice pack of claim 1, wherein one sheet is attached juxtaposed to one each of the bag portion outer walls.

6. The disposable ice pack of claim 5, wherein the one sheet of fluid absorbable material is attached to each of the bag portion outer walls by a heat seal.

7. The disposable ice pack of claim 6, wherein the heat seal is disposed along each bag portion side edge in parallel relationship thereto between each bag portion outer wall and each sheet of fluid absorbable material.

8. The disposable ice pack of claim 7, wherein an additional heat seal is provided along the bag portion bottom end in parallel relationship thereto between each bag portion outer wall and each sheet of fluid absorbable material.

9. The disposable ice pack of claim 1, wherein the thickness of the bag portion is generally equal to the thickness of the one sheet of fluid absorbable material.

10. The disposable ice pack of claim 1, wherein the thickness of the bag portion is in the range of 1¼ mils to 2½ mils.

11. The disposable ice pack of claim 1, wherein the thickness of one sheet of fluid absorbable material is in the range of 1¼ mils to 2½ mils.

12. The disposable ice pack of claim 1, wherein the frozen material is chosen from the group including ice and a pliable container of a freezable chemical composition.

13. The disposable ice pack of claim 1, further comprising a plurality of tie-straps for attaching the disposable ice pack to the traumatized area of the person's body.

14. The disposable ice pack of claim 13, wherein four tie-straps are employed, one each attached by a heat seal at four opposed corners of the ice pack between one of the bag portion outer walls and the at least one sheet of fluid absorbable material.

15. A disposable ice pack for receiving and retaining ice and for compressing against an area of a person's body that has been traumatized, the disposable ice pack consisting of:
   a) a generally square-shaped bag portion having four side edges, including a sealable open top end, a closed bottom end and a pair of opposed side edges forming an inner cavity, a closure mechanism disposed along inner surfaces of the top end providing a water tight seal to the ice pack, and a pair of outer walls, each side edge disposed at an adjacent side edge at a ninety-degree angle;
   b) a sheet consisting of one layer of fluid absorbable two fiber cloth material, attached juxtaposed to each of the bag. portion outer walls, each fluid absorbable material having a dimension slightly less than the outer walls of the four edge generally square-shaped bag portion such that each side edge of the sheet material is positioned adjacent and parallel to one of the bag portion four side edges at a distance which is equal around all four side edges of the sheet material and bag portion, one of the sheets of fluid absorbable material making contact with the person's traumatized body area and absorbing any body fluids seeping therefrom; and
   c) the inner cavity receiving and retaining the ice.

16. The disposable ice pack of claim 15, wherein the bag portion is constructed of polyethylene.

17. The disposable ice pack of claim 15, wherein each of the sheets of fluid absorbable material is constructed of a two fiber cloth comprising a first fiber of alpha-cellulose and a second fiber of polyester.

18. The disposable iced pack of claim 15, wherein each of the sheets of fluid absorbable material is attached to the bag portion outer walls by a heat seal along the pair of opposed side edges and the bottom end.

19. The disposable ice pack of claim 15, wherein the thickness of the bag portion is in the range of 1¼ mils to 2½ mils and the thickness of each of the two sheets of fluid absorbable material is in the range of 1¼ mils to 2½ mils.

20. The disposable ice pack of claim 15, further comprising a plurality of tie-straps for attaching the disposable ice pack to the traumatized area of the person's body, one each attached by a heat seal at four opposed corners of the ice pack between one of the bag portion outer walls and one of the two sheets of fluid absorbable material.

* * * * *